United States Patent [19]
Gorman et al.

[11] Patent Number: 5,521,169
[45] Date of Patent: May 28, 1996

[54] ASCOSTEROSIDE AND ANALOGS THEREOF USEFUL IN ANTIFUNGAL COMPOSITIONS FOR METHODS OF TREATING INFECTIONS AND INHIBITION OF FUNGAL GROWTH

[75] Inventors: Jessica A. Gorman, Yardley, Pa.; Joseph O'Sullivan, Belle Mead, N.J.; John E. Leet; Stephen W. Mamber, both of Wallingford, Conn.

[73] Assignee: Bristol-Myers Squibb Company, Princeton, N.J.

[21] Appl. No.: 181,688

[22] Filed: Jan. 14, 1994

[51] Int. Cl.$^6$ .............. C12P 1/02; A61K 31/56; C07J 9/00
[52] U.S. Cl. .............. 514/182; 435/171; 536/1.11; 536/4.1; 536/5; 552/526; 552/540
[58] Field of Search .............. 514/182; 435/171; 552/526, 540; 536/1.11, 4.1, 5

[56] References Cited

FOREIGN PATENT DOCUMENTS

| 504711A | 9/1992 | European Pat. Off. . |
| 4115490A1 | 11/1992 | Germany . |
| 03119993 | 5/1991 | Japan . |
| 04046188 | 2/1992 | Japan . |

OTHER PUBLICATIONS

Wehrli, et al., "Structure of the novel steroidal antibiotic squalamine determined by two-dimensional NMR spectroscopy." Steroids 58:370–378 (1993).
S. Inouye et al., J. Syn. Org. Chem. Japan, "Current Antifungal Antibiotics", vol. 51, No. 4, pp. 327–349, 1993.
The Merck Index, 9th Ed., 6735. Ouabain, p. 896 (1976).
CA Selects: Fungicides, B. Schlegel, et al., "A novel antifungal antibiotic manufactured by cultures of Tolypocladium or Sesquicillopsis", Issue 3, 1993, 118:37554q (abstract of DE 4115490).
L. Minale et al., Progress in the Chemistry of Organic Natural Products, Edited by Herz et al., Springer–Verlag, Wien, N.Y., 1993, "Steroidal Oligoglycosides and Polyhydroxysteriods from Echinoderms", pp. 75–77 and pp. 285–297.

Primary Examiner—John W. Rollins
Assistant Examiner—Deborah K. Ware
Attorney, Agent, or Firm—Suzanne E. Babajko

[57] ABSTRACT

Ascosteroside, obtainable by cultivation of a strain of *Ascotricha amphitricha* A.T.C.C. No. 74237, analogs thereof and salts and prodrugs of these compounds. The compounds have antifungal activity for use in a method for treating and preventing a fungal infection. Further, the compounds are useful in a method for inhibiting fungal growth.

8 Claims, 4 Drawing Sheets

ASCOSTEROSIDE AND ANALOGS THEREOF USEFUL IN ANTIFUNGAL COMPOSITIONS FOR METHODS OF TREATING INFECTIONS AND INHIBITION OF FUNGAL GROWTH

FIELD OF THE INVENTION

The present invention relates to a novel class of antifungal antibiotic compounds, including the compound designated herein as ascosteroside, analogs of this compound, and salts and prodrugs thereof. Ascosteroside may be obtained by cultivation of a strain of *Ascotricha amphitricha*. The present invention also relates to methods of preparing, compositions containing and methods of using the inventive compounds, and to the novel strain of *Ascotricha amphitricha*.

SUMMARY OF THE INVENTION

Cultivation of a strain of the microorganism *Ascotricha amphitricha*, which has been deposited in the American Type Culture Collection as A.T.C.C. No. 74237, yields the novel compound hereinafter referred to as ascosteroside. This compound has been found to have antibiotic activity, particularly antifungal activity. Ascosteroside has been analyzed and has been found to have the chemical structure:

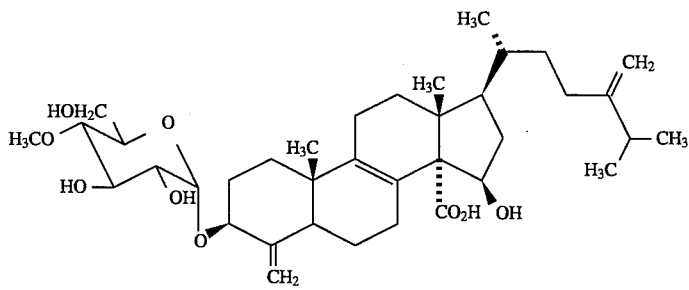

corresponding to the name 15-hydroxy-4-methylene- 3-(4-O-methyl-α-D-glucopyranosyl)-3β,5α-ergosta- 8,24(28)-diene-14-carboxylic acid. Analogs of this compound, such as salts, esters and amides thereof as described below, are also expected to exhibit the aforementioned antifungal activity.

The present invention therefore provides the novel compounds of the following formula I:

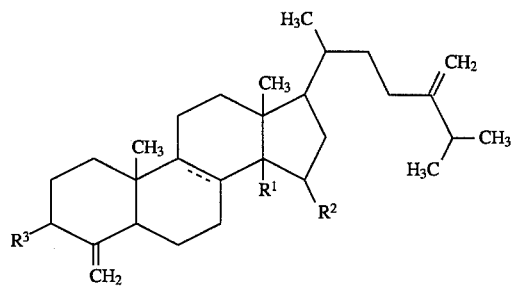

wherein $R^1$ is —C(O)—OR$^4$, —C(O)N(R$^4$)$_2$ or —PO$_4$(R$^4$)$_2$;

$R^2$ is hydroxyl, —O—C(O)—R$^5$, —PO$_4$(R$^4$)$_2$ or —SO$_4$(R$^4$);

$R^3$ is hydroxyl, —O—C(O)—R$^5$, —PO$_4$(R$^4$)$_2$, —SO$_4$(R$^4$) or a sugar moiety;

each $R^4$ is independently hydrogen, alkyl or aryl;

each $R^5$ is independently alkyl or aryl; and the dotted line denotes an optional double bond; as well as salts and/or prodrugs thereof. It is understood that all stereoisomers of the compounds of the present invention are contemplated herein, whether alone (that is, substantially free of other isomers), in a mixture of certain stereoisomers (for example, as a racemate) or in any other mixture thereof.

The compounds of the present invention possess antibiotic activity against a variety of microorganisms, and may therefore be used, for example, to prevent or treat fungal infections in animals, particularly humans, as well as to serve as disinfectants for suppressing fungal growth, for example, on surfaces such as those of surgical instruments.

The present invention therefore also provides novel compositions comprising, and methods of using, the inventive compounds as antifungal agents, as well as methods of making the inventive compounds, and the novel strain of *Ascotricha amphitricha* described herein.

DETAILED DESCRIPTION OF THE INVENTION

Figure 1:
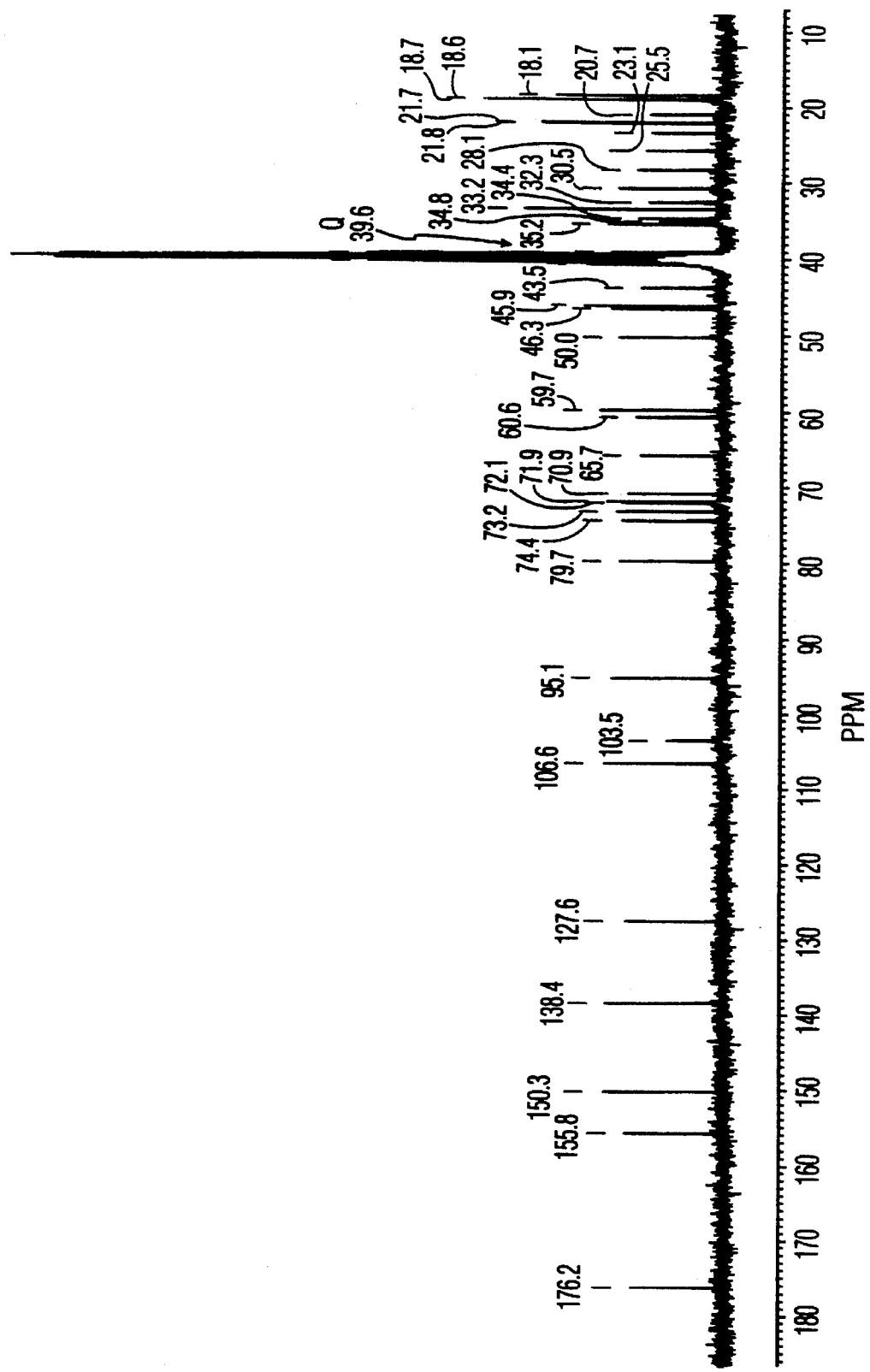
FIG. 1 shows the $^{13}$C NMR spectrum of ascosteroside (DMSO).
Figure 2:
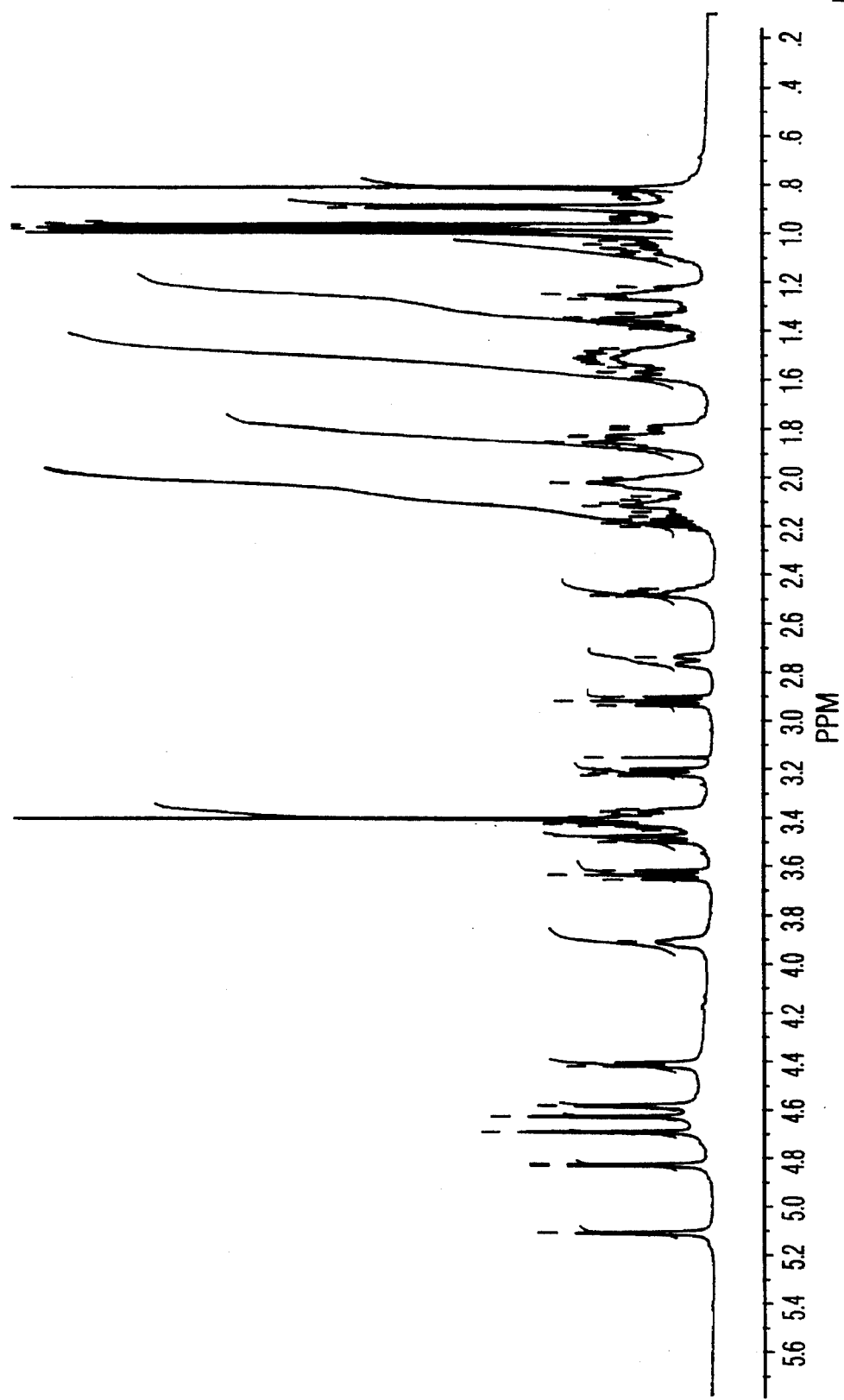
FIG. 2 shows the $^1$H NMR spectrum of ascosteroside (DMSO).
Figure 3:
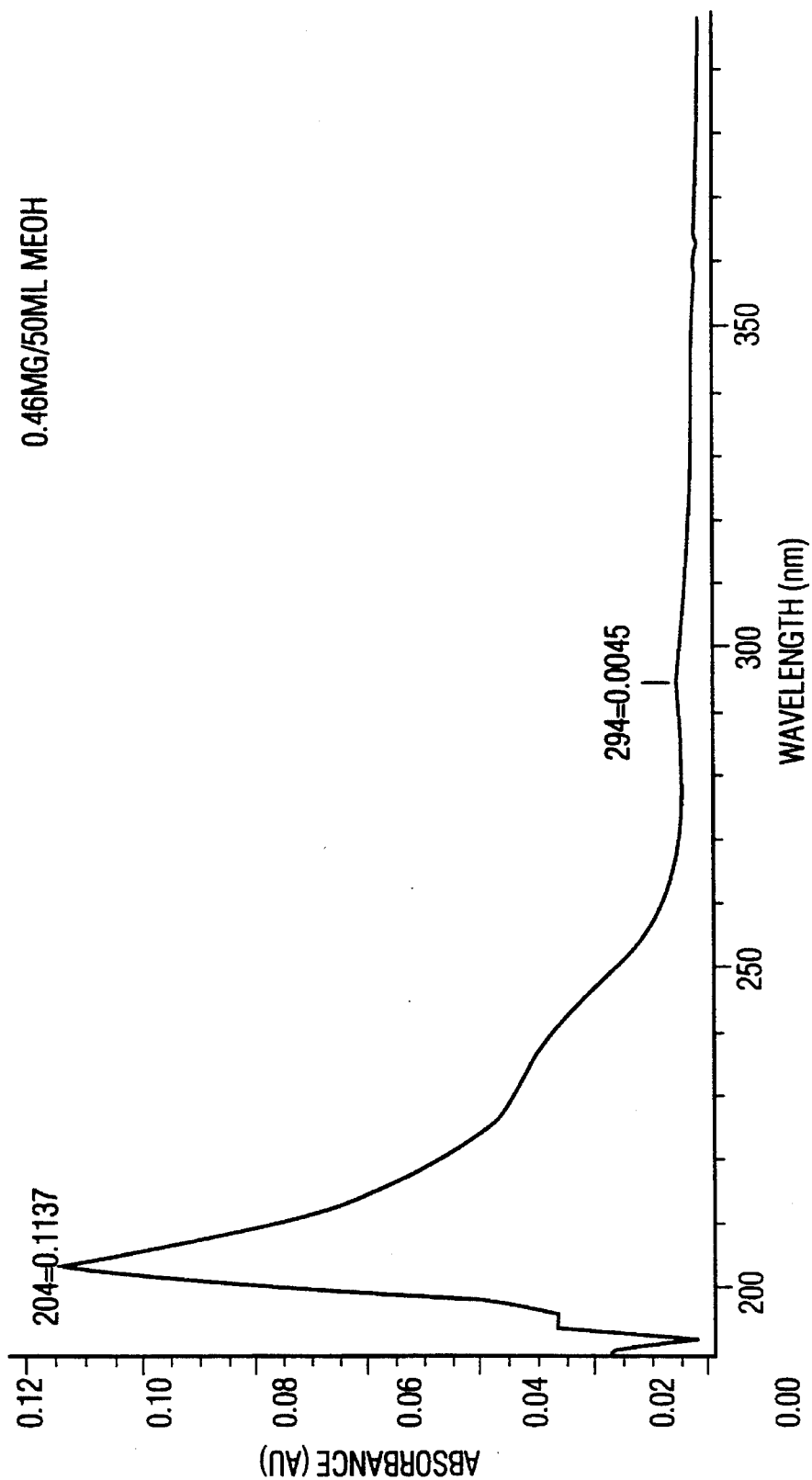
FIG. 3 shows the ultraviolet (UV) spectrum of ascosteroside in methanol.
Figure 4:
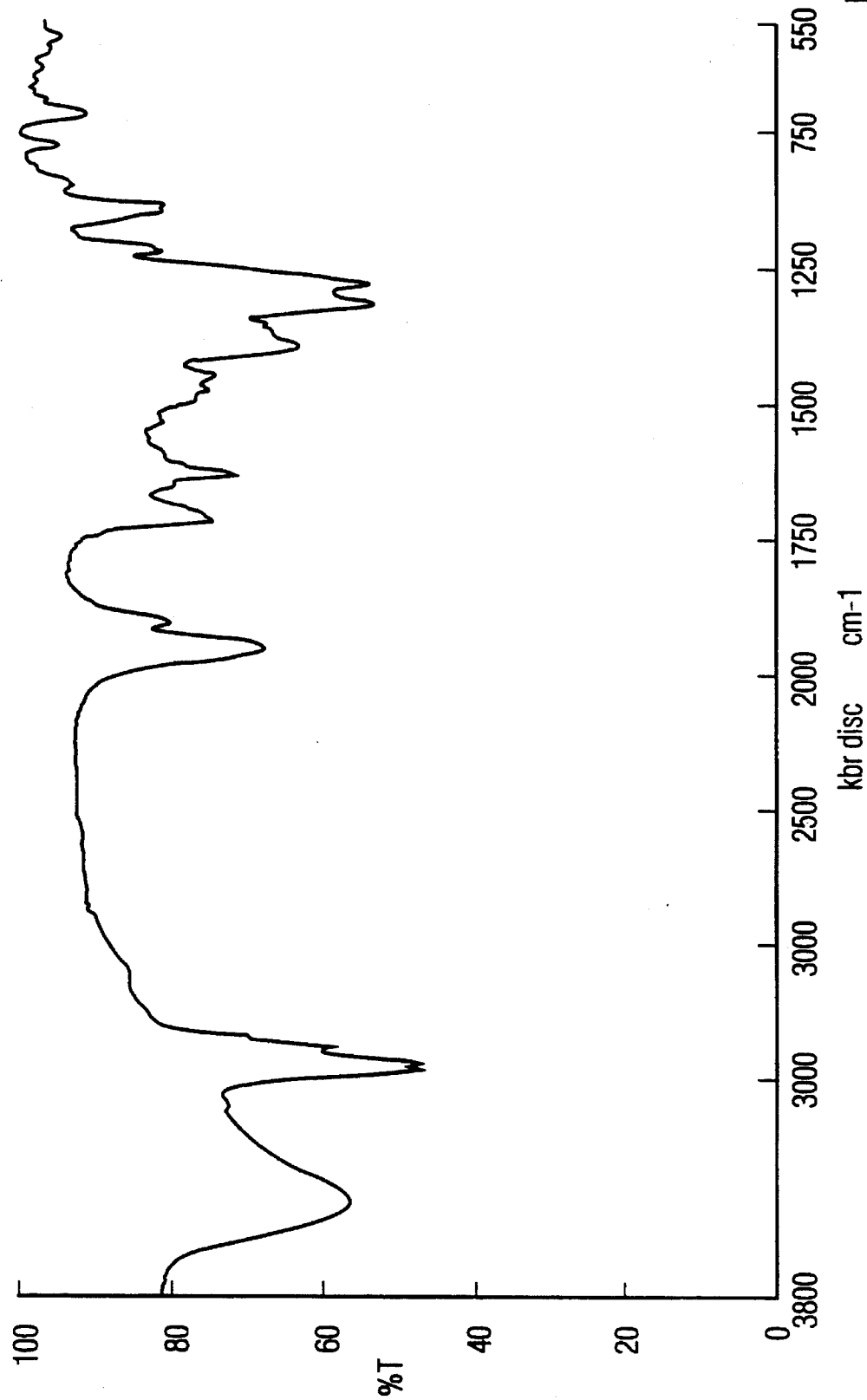
FIG. 4 shows the infrared spectrum of ascosteroside (KBr).

The present invention is described further as follows.

The Microorganism

The microorganism which may be used for the production of ascosteroside is a strain of *Ascotricha amphitricha*, which strain was isolated from a soil sample obtained in Kenya. A subculture of the microorganism may be obtained from the permanent collection of the American Type Culture Collection, 12301 Parklawn Drive, Rockville, Md. 20852, where it was deposited on Aug. 25, 1993 and received the accession number A.T.C.C. No. 74237. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce ascosteroside.

Isolation of the microorganism *Ascotricha amphitricha* A.T.C.C. No. 74237 from a soil sample in which it is present may be accomplished by first suspending the soil sample in a sterile diluent such as buffered saline containing 0.01% gelatin and shaking vigorously. A dilution of this suspension may then be plated onto a nutrient medium. The composition of an exemplary such medium is:

| Soil extract solution* | 200 mL |
|---|---|
| Dextrose | 10 g |
| Peptone | 5 g |
| Agar | 18 g |
| Tap water | 800 mL |
| Lactic acid** | 1 mL |

*The soil extract solution is made by boiling a suspension of soil in water (1:2, w/v) for 1 hour and filtering the cooled extract.
**Sterilized by filtration and added to the medium that has already been autoclaved at 121° C. for 20 minutes.

After 4 days incubation at room temperature (at or about 25° C.), the colonies of *Ascotricha amphitricha* A.T.C.C. No. 74237 may be isolated from the plated soil. The isolated colonies may then be transferred ("picked off") onto a potato-dextrose agar medium having the following composition:

| Potato infusion | 200.0 g |
|---|---|
| Dextrose | 20.0 g |
| Agar | 15.0 g |
| Deionized water | to 1000.0 ml |

Colonies of *Ascotricha amphitricha* A.T.C.C. No. 74237 grown on potato-dextrose agar show a white mycelium with dark ascocarps forming among the mycelium. The reverse color is dark. Perithecia develop rapidly on oat-meal and corn-meal agars. The perithecia arise from the mycelium, are ostiolate with a short discrete neck, and are dark and globose. Terminal hairs are slender, whip-like, flexuous, mostly simple with occasional dichotomous branching. They turn brown with age. No lateral hairs are observed.

The ascogonium forms a helical coil, with open spirals in several whorls. Asci are cylindrical, containing 8 thin walled ascospores, measuring about 50μ by 6μ. They do not turn blue with Meltzer's iodine stain; they deliquesce after the spores are mature. Ascospores are ellipsoidal with an equatorial furrow. They measure about 6μ by 11μ, are uniseriate, becoming dark olive brown at maturity.

The conidial (or asexual) stage is a member of the genus Dycima. The conidia arise in clusters on pale conidiophores, appearing smooth or slightly roughened, hyaline, irregularly globose to ellipsoidal, measuring about 2.2μ by 3.5μ.

These characteristics serve to identify the organism as *Ascotricha amphitricha*, in accordance with the description of this organism (Chivers, A. H., "A monograph of the genera Chaetomium and Ascotricha", Memoirs of the Torrey Botanical Club, Vol 14:3 (1915); Hawksworth, D. L., "A revision of the genus Ascotricha", Ber., Mycological Papers #126, pp. 1–33 (1971)) .

The present invention provides the above novel strain of *Ascotricha amphitricha* designated by A.T.C.C. No. 74237, which may be isolated from soil such as by the cultivation and isolation methods described herein. Also provided are organisms which have the identifying characteristics of the strain designated by A.T.C.C. No. 74237 as discussed above, and which are capable of producing ascosteroside. Such organisms include those originally designated as *Ascotricha amphitricha* A.T.C.C. No. 74237 which have been modified by physical, chemical, or biological means. Substantially pure, especially biologically pure, cultures of the organisms described herein are preferred.

The Novel Compounds

The novel antibiotic ascosteroside may be produced by fermentation of *Ascotricha amphitricha* A.T.C.C. No. 74237, or by a microorganism having the identifying characteristics of the aforementioned *Ascotricha amphitricha* and which is capable of producing said compound, and isolating said compound from the fermentation broth. For example, ascosteroside may be produced by cultivation of *Ascotricha amphitricha* A.T.C.C. No. 74237 at or about a temperature of 18° C. to 35° C., preferably at 28° C., under submerged aerobic conditions in an aqueous nutrient medium containing assimilable sources of carbon and nitrogen and other optional nutrients. The fermentation is preferably carried out until substantial antibiotic activity is imparted to the medium, usually about 96 to 144 hours. The fermentation, as well as the subsequent isolation steps, may be monitored by means of a conventional well agar diffusion assay with either *Saccharomyces cerevisiae* or *Candida albicans* as the assay organism, or by HPLC column chromatography on C18 silica gel, eluting with a gradient system of acetonitrile and 0.1M potassium phosphate buffer (pH 3.5), as described by Hook et al., *J. Chromat.*, 385:99 (1987).

Ascosteroside may be isolated and purified by means of art-recognized techniques from the fermentation broth. The antibiotic may be extracted from the broth into an organic solvent, preferably ethyl acetate. The organic phase can be separated and concentrated in vacuo to a residue which may then be dissolved in 10% aqueous methanol. The aqueous methanolic solution may be washed with hexane, and the hexane layers discarded. The aqueous phase can then be diluted with water so that the water content is 35% of the total volume, followed by extraction with chloroform which had previously been equilibrated with 35% water in methanol. The chloroform layer may be separated and concentrated in vacuo to yield a residue. Further purification may be effected by chromatography of the residue on Sephadex LH-20 (chromatography support; gel filtration medium) with a 1:1 mixture of chloroform:methanol, followed by reverse phase high pressure liquid chromatography to provide pure ascosteroside.

The term "salts", as used herein, denotes acidic and/or basic salts, formed with inorganic or organic acids and/or bases. While pharmaceutically acceptable salts are preferred, particularly when employing the compounds of the invention as medicaments, other salts find utility, for example, in processing these compounds, or where non-medicament-type uses are contemplated. Salts of the inventive compounds may be prepared by art-recognized techniques. For example, ascosteroside is a weak acid and will form salts with inorganic and organic bases. Illustrative salts include those of monovalent inorganic cations (e.g., sodium or potassium), divalent inorganic cations (e.g., calcium or magnesium), organic cations (e.g., quaternary ammonium salts), and the like.

The term "prodrug", as used herein, denotes compounds which, in vivo, undergo chemical conversion to a compound of the formula I, such as ascosteroside, or salts thereof. Prodrug compounds may be prepared by art-recognized techniques such as those described in *Design of Prodrugs*, edited by H. Bundgaard (Elsevier, 1985).

The term "alkyl", as used herein, denotes straight and branched chain hydrocarbon groups having 1 to 8 carbon atoms such as methyl, ethyl, propyl, isopropyl, n-butyl, t-butyl, isobutyl, n-pentyl, n-hexyl, isohexyl, n-heptyl, n-octyl and the like, which groups may be unsubstituted or substituted with groups such as aryl, hydroxyl, amino, halo (i.e., chlorine, fluorine, bromine or iodine), nitro, and the like.

The term "aryl", as used herein, denotes phenyl, biphenyl or naphthyl, each of which may be unsubstituted or substituted with groups such as alkyl, hydroxyl, amino, halo, nitro, and the like.

The term "sugar moiety", as used herein, denotes a sugar bonded through a glycosidic linkage (—O—). Exemplary sugar moieties include glucose, galactose, and the like, each bonded through a glycosidic linkage. The term "sugar moiety" also includes sugars bonded through a glycosidic linkage which have been modified, such as by acylation at a hydroxyl group thereof.

Ascosteroside may be prepared as described above. Exemplary methods for the preparation of other compounds of the formula I include those involving the modification of ascosteroside, such as by employing art-recognized techniques. Illustrative such techniques are those described in *Methods in Carbohydrate Chemistry: Vol.* 1, edited be R. L. Whistler, M. L. Wolfrom (Academic Press, 1962), Vol. 6, edited by R. L. Whistler, J. N. BeMiller (Academic Press, 1972); and *Modern Synthetic Reactions*, 2nd ed., by H. O. House (Benjamin/Cummings Publishing Co. 1972). For example, ascosteroside may be hydrolyzed by acidic methanolysis to form the aglycone ($R^3$ is hydroxyl). $R^2$ and/or $R^3$ groups which are hydroxyl may be converted to the group —O—C(O)—$R^5$ by esterification (e.g., by contact with an acylating agent such as a carboxylic acid chloride). Alternatively, the $R^2$ and/or $R^3$ groups may be converted to the phosphate group —$PO_4(R^4)_2$ by phosphorylation or to the sulfate group —$SO_4(R^4)$ by sulfation. Sugars other than that found on ascosteroside may be added to the aforementioned agylcone of ascosteroside by glycosylation to form compounds where $R^3$ is a sugar moiety.

Where $R^1$ is carboxyl, that group may be converted to the group —C(O)—$OR^4$ where $R^4$ is alkyl or aryl by esterification (e.g., by diazomethane methylation or by conversion to the acid chloride followed by reaction with the appropriate alcohol); to the group —$CON(R^4)_2$ by amide formation (e.g., by conversion to the acid chloride followed by reaction with the appropriate amine); or to the group —$PO_4(R^4)_2$ by phosphorylation.

The ethylenic bond in the ring system of ascosteroside may be converted to a single bond by hydrogenation, such as by low pressure catalytic hydrogenation, to form a fully saturated ring system.

Hydroxyl or other groups which are not to be converted may optionally be protected.

Utility

The novel compounds of the present invention include the compounds of formula I and salts and prodrugs thereof. Ascosteroside is a preferred compound of the formula I.

It is preferred that the inventive compounds have a degree of purity such that they are suitable for use as antibiotic agents. A particularly preferred embodiment of the present invention provides a compound of the formula I, or a salt or prodrug thereof, in its pure or substantially pure state. The pure or substantially pure compounds are preferably employed in preparing compositions such as those of the present invention. Further, the pure or substantially pure compounds, alone or as used in compositions exemplified by those described herein, are preferably employed in the methods of the present invention. It is understood that a single, or two or more, compound(s) of the present invention may be employed in any of the compositions or methods described herein.

The inventive compounds are useful as antimicrobial agents, having utility in inhibiting the growth of microorganisms. The inventive compounds are particularly useful as antifungal agents, having activity against a variety of fungi. Thus, the compounds of the present invention may be employed in utilities suitable for such antifungal agents.

The inventive compounds may, for example, be used in treating a host infected with a fungus, or in preventing infection of said host by said fungus, comprising the step of administering to the host a compound of the formula I, or a physiologically tolerated salt or prodrug thereof in an amount effective for said prevention or treatment. Treatment of such infections according to the present invention includes both mitigation as well as elimination thereof.

Hosts administered the inventive compounds may be plants or animals, particularly animals such as dogs, cats and other domestic mammals and, especially, humans. The dosage form and mode of administration, as well as the dosage amount, may be selected by one of ordinary skill in the art. The dosage amount will vary with the severity of the infection, and with the size and species of the host. Exemplary daily dosages for an adult human are those within the range of from about 250 mg to about 2 g/day. Administration to a mammalian host may, for example, be oral, topical, rectal or parenteral. Administration to a plant host may be accomplished by, for example, application to seed, foliage or other plant part, or to the soil.

Compositions are also provided by the present invention which comprise a compound of the formula I, or a physiologically tolerated salt or prodrug thereof, in an amount effective for the prevention or treatment of infection by a fungus, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to one of ordinary skill in the art. Prevention or treatment of simultaneous infections by more than one fungus is, of course, contemplated.

The inventive compounds may also be employed as antimicrobial agents useful in inhibiting the growth of microorganisms present on a surface or in a medium outside a living host. The present invention therefore provides a method for inhibiting the growth of at least one fungus present on a surface or in a medium, comprising the step of contacting the surface or medium with a compound of the formula I, or a salt thereof, in an amount effective for the inhibition. Thus, the inventive compounds may be employed, for example, as disinfectants for surface treatments, such as disinfection of surgical instruments, or as preservatives for a variety of solid and liquid media susceptible to microbial growth. Suitable amounts of the inventive compounds may be determined by methods known to one of ordinary skill in the art. Compositions comprising a compound of the formula I or a salt thereof in an amount effective for inhibiting the growth of at least one fungus, and a vehicle or diluent, are also provided by the present invention.

The following examples further illustrate the invention, and are not intended to in any way limit the present claims.

EXAMPLE 1

Preparation of Ascosteroside

A frozen vegetative culture of *Ascotricha amphitricha* A.T.C.C. No. 74237 was prepared by using the growth from potato-dextrose agar slants, the composition of which is described above, to inoculate 100 ml of vegetative medium contained in 500 mL Erlenmeyer flasks. The composition of the vegetative medium was:

| | |
|---|---|
| Tryptone | 5.0 g |
| Malt extract | 3.0 g |
| Glucose | 10.0 g |
| Yeast extract | 3.0 g |
| Deionized water | to 1000 mL |

The medium was sterilized at 121° C. for 20 minutes prior to use.

After incubation at 28° C. for 72 hours on a rotary shaker operating at 250 rpm, the resulting growth was mixed with an equal volume of a sterile solution consisting of:

| | |
|---|---|
| Sucrose | 100 g |
| Glycerol | 200 g |
| Deionized water | to 1000 mL |

Four mL portions of this suspension were dispensed into sterile cryogenic tubes that were immersed in a dry ice-acetone bath. The frozen cultures so obtained were then stored at −80° C., and maintained at −80° C. as frozen vegetative cultures.

For shake flask production, 4 mL of frozen vegetative culture were transferred to 100 mL of medium in a 500 mL Erlenmeyer flask. The composition of the medium was that described above for the vegetative medium. The inoculated medium was incubated for 72 hours at 28° C. on a rotary shaker operating at 250 rpm. Two ml of the resulting growth was then used to inoculate 100 ml of the production medium in each of a number of 500 ml Erlenmeyer flasks (200 flasks total). The composition of the production medium was:

| | |
|---|---|
| Tryptone | 5.0 g |
| Malt extract | 3.0 g |
| Glucose | 10.0 g |
| Yeast extract | 3.0 g |
| Deionized water | to 1000 ml |

The production cultures were incubated at 28° C. and 250 rpm for 6 days. After 6 days the broth from the 200 Erlenmeyer flasks containing 100 ml each was harvested and pooled.

For production in a fermentor, 2 ml of the vegetative culture was inoculated into a 500 ml Erlenmeyer flask containing 100 ml of the vegetative medium. This second seed culture was incubated at 28° C. and 250 rpm for 3 days. Two second seed cultures (200 ml) were transferred to a B. Braun Biostat ED fermentor containing 10 liters of the production medium. The fermentation was carried out for 5 days at 28° C., during which time the broth was agitated at the rate of 500 rpm and aerated at the rate of 1 volume of air per minute. The back pressure of the fermentor was set at 0.4 bar.

Ten liters of ethyl acetate were added to the pooled broths, or to the fermentor broth, and the mixture stirred for 1 hour at room temperature. After the addition of approximately 4 liters (1.5 kg) of Dicalite (diatomaceous earth), the suspension was filtered by vacuum filtration and the colorless ethyl acetate layer separated. The ethyl acetate layer was evaporated in vacuo to dryness in a rotary evaporator to yield approximately 2 g of residue.

The residue was dissolved in 10 ml of 10% aqueous methanol and the solution was then washed 3 times with equal volumes of hexane. The hexane layers were discarded. The aqueous methanol phase was diluted to 35% water in methanol by the addition of 3.8 ml of water and extracted 3 times with equal volumes of chloroform. The chloroform had been previously saturated with 35% water in methanol. Concentration of the chloroform layer to dryness in a rotary evaporator gave a residue of 0.56 g. This residue was dissolved in 2 ml of a mixture of chloroform:methanol 1:1, and applied to 100 g of Sephadex LH-20 packed in the same solvent mixture and contained in a column (3×100 cm). The column was eluted at a flow rate of 2–3 ml/min with a solvent mixture of the same composition as used to dissolve the sample and pack the column. Eight ml fractions were collected and monitored by means of thin layer chromatography on silica gel, with a mixture of chloroform:methanol, 9:1, as the developing solvent. The desired fractions were those with materials exhibiting an $R_f$ of approximately 0.12 and giving a dark blue-gray spot when sprayed with a solution of cerric sulfate and heated. These were pooled and the solvent removed by evaporation in vacuo.

Final purification of the residue just obtained was effected by preparative high pressure liquid chromatography. A 5 mg portion, dissolved in 0.5 mL of methanol, was applied to a reverse phase HPLC column (Dynamax C18, 21.4 mm i.d.×25 cm length, 8 micron particle size, 60 A pore size) and eluted with a mobile phase of acetonitrile-water, 1:1, followed by a linear gradient to 100% acetonitrile over a time period of 30 minutes at a flow rate of 10 ml/min. UV detection (230 nm) was used. The major active peak (22 min) was collected and the solvent removed in vacuo to yield 19 mg of pure ascosteroside.

Ascosteroside, a colorless, amorphous solid, has been found to have the following characteristics: accurate mass measurement of the M+Na$^+$ ion in the Fast Atom Bombardment Spectrum (FAB-MS) in a m-nitrobenzoyl alcohol matrix yielded a value of 669.3964, for a molecular weight of 646.4066 for the free acid. Thus, the empirical formula of ascosteroside is $C_{37}H_{58}O_9$. The UV spectrum, recorded in methanol, showed absorption maxima (log ε) at values of 204 (3.90), 235 sh (3.32) and 294 (2.50) nm. Specific rotation of ascosteroside: $[\alpha]_D = +43°$ (c 0.2, methanol). Absorption maxima (cm$^{-1}$) of the major bands in the infrared spectrum of ascosteroside recorded in KBr were: 3448, 2960, 2934, 1700, 1652, 1466, 1382, 1196, 1146, 1066, 1030, 972 and 886. In the $^1$H NMR spectrum (500 MHz), the observed chemical shifts relative to 30 DMSO-d$_6$ signal 2.49 were: 0.82 (s, 3H), 0.89 (d, 3H, J=6.4 Hz), 0.97 (d, 3H, J=6.8 Hz), 0.98 (d, 3H, J=6.8 Hz), 1.00 (s, 3H), 1.08 (m, 1H), 1.26 (m, 2H), 1.36 (m, 2H), 1.52 (m, 4H), 1.59 (m, 1H), 1.85 (m, 4H), 2.03 (m, 3H), 2.12 (m, 2H), 2.19 (sept., 1H, J=6.8 Hz), 2.49 (m, 1H), 2.75 (d br, 1H, J=13.2 Hz), 2.92 (t, 1H, J=9.2 Hz), 3.21 (dd, 1H, j=9.6, 3.5 Hz), 3.40 (m, 2H), 3.41 (s, 3H), 3.49 (d, 1H, J=11.4 Hz), 3.64 (t, 1H, J=9.2 Hz), 3.91 (m, 1H), 4.41 (d, 1H, J=7.1 Hz), 4.59 (s, 1H), 4.63 (s, 1H), 4.70 (s, 1H), 4.83 (d, 1H, J=3.5 Hz), 5.11 (s, 1H). The $^{13}$C NMR spectrum (125 MHz) in DMSO-d$_6$ of ascosteroside is as set forth in the following Table 1.

TABLE 1

$^{13}C$ NMR data of Ascosteroside (in DMSO-$d_6$)

| Signal | PPM | Multiplicity |
| --- | --- | --- |
| 1 | 18.1 | q |
| 2 | 18.6 | q |
| 3 | 18.7 | q |
| 4 | 20.7 | t |
| 5 | 21.7 | q |
| 6 | 21.8 | q |
| 7 | 23.1 | t |
| 8 | 25.5 | t |
| 9 | 28.1 | t |
| 10 | 30.5 | t |
| 11 | 32.3 | t |
| 12 | 33.2 | d |
| 13 | 34.4 | t |
| 14 | 34.8 | t |
| 15 | 35.2 | d |
| 16 | 39.6 | s |
| 17 | 43.5 | t |
| 18 | 45.9 | s |
| 19 | 46.3 | d |
| 20 | 50.0 | d |
| 21 | 59.7 | q |
| 22 | 60.6 | t |
| 23 | 65.7 | s |
| 24 | 70.9 | d |
| 25 | 71.9 | d |
| 26 | 72.1 | d |
| 27 | 73.2 | d |
| 28 | 74.4 | d |
| 29 | 79.7 | d |
| 30 | 95.1 | d |
| 31 | 103.5 | t |
| 32 | 106.6 | t |
| 33 | 127.6 | s |
| 34 | 138.4 | s |
| 35 | 150.3 | s |
| 36 | 155.8 | s |
| 37 | 176.2 | s |

EXAMPLE 2

Biological Activity of Ascosteroside

The following methodology was used to demonstrate the activity of ascosteroside against a panel of microorganisms selected from the Bristol Myers Squibb Culture Collection.

For activity studies with yeasts, the test organisms were grown in a medium containing:

| | |
| --- | --- |
| Tryptone | 5 g |
| Malt extract | 3 g |
| Yeast extract | 3 g |
| Glucose | 10 g |
| Distilled water qs to | 1000 mL |

The medium was sterilized at 121° C. for 20 minutes before use. After inoculation with the test organism, the medium was incubated for 18 to 24 hours at 30° C. on a rotary shaker operating at 250 rpm with a 0.5 cm throw. A 0.25 mL portion of the growth was used to inoculate 250 mL of the same medium supplemented with 1.5% agar that had been melted and cooled in a temperature controlled water bath to 48° C. After mixing, 25 mL of the seeded agar was placed in each of several Petri dishes, and the medium allowed to harden. At that time, wells were cut into the agar with a sterile, 4 mm diameter cork-borer. To each well was added 6 μl of solution containing an amount of ascosteroside (5 μg per well) dissolved in an appropriate solvent. The plates were incubated at 30° C. for 18 to 24 hours and then examined. Activity was observed as a zone of inhibition of growth about each well.

The results of the activity determinations for ascosteroside were as follows:

| Fungal Microorganism* | Zone Diameter (mm) |
| --- | --- |
| Saccharomyces cerevisiae SGY1242 | 20 |
| Saccharomyces cerevisiae SGY1243 | 14 |
| Candida albicans SC5314 | 21 |
| Candida albicans SC8159 | 20 |
| Candida glabrata SC9342 | 21 |
| Trichophyton mentagrophytes SC2627 | 20 |
| Aspergillus nidulans SC12914 | 20 |

*SGY or SC denotes the strain of the microorganism from the Squibb Culture Collection

EXAMPLE 3

Preparation of Ascosteroside Methyl Ester

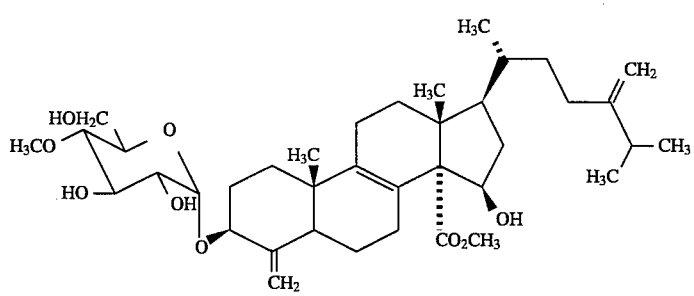

Ascosteroside (21 mg, 0.03 mmol) was dissolved in a few drops of methanol and mixed with excess etherial diazomethane (3 ml, prepared from Diazald reagent according to Aldrich Co. technical bulletin AL-121, 1982). The contents were allowed to stand at 10° C. for 18 hours. The mixture was concentrated under nitrogen gas and dried. Final purification was accomplished by preparative HPLC (C-18) as described in Example 1, using a mobile phase of acetonitrile-water 7:3, followed by a linear gradient to 100% acetonitrile over 30 minutes. The major peak (24 min) was collected and solvent removed in vacuo to yield 12 mg of pure ascosteroside methyl ester: $C_{38}H_{60}O_9$: TLC $R_f$ 0.35 (CHCl$_3$—MeOH 9:1); HRFABMS m/z 683.4113 ([M+Na]$^+$;

calcd 683.4135); IR $\gamma_{max}$ (KBr) 3440, 2936, 2874, 1710, 1646, 1464, 1384, 1204, 1140, 1068, 1030, 972, 896, 778 cm$^{-1}$; $^1$H-NMR (500 MHz, DMSO-d$_6$) δ 0.81 (s, 3H), 0.88 (d, J=6.4 Hz, 3H), 0.97 (d, J=6.8 Hz, 3H), 0.98 (d, J=6.8 Hz, 3H), 1.01 (s, 3H), 1.06 (m, 1H), 1.23 (m, 1H), 1.27 (m, 1H), 1.28 (m, 1H), 1.39 (dd, J=9.2, 13.4 Hz, 1H), 1.48 (m, 1H), 1.50 (m, 1H), 1.57 (m, 1H), 1.62 (dd, J=8.4, 12.4 Hz, 1H), 1.77 (m, 1H), 1.80 (m, 1H), 1.83 (m, 1H), 1.85 (m, 1H), 1.89 (m, 1H), 2.00 (m, 1H), 2.03 (m, 1H), 2.04 (m, 1H), 2.14 (m, 1H), 2.19 (sept, J=6.8 Hz, 1H), 2.52 (m, 1H), 2.74 (d br, J=13.4 Hz, 1H), 2.93 (t, J=9.2 Hz, 1H), 3.22 (dd, J=3.0, 9.5 Hz, 1H), 3.38 (dd, J=1.8, 4.6 Hz, 1H), 3.41 (s, 3H), 3.43 (m, 1H), 3.47 (m, 1H), 3.51 (s, 3H), 3.64 (t, J=9.2 Hz, 1H), 3.91 (m, 1H), 4.38 (t, J=5.5 Hz, 1H), 4.52 (t, J=5.5 Hz, 1H), 4.58 (s, 1H), 4.63 (s, 1H) 4.69 (s, 1H), 4.77 (d, J=4.8 Hz, 1H), 4.83 (d, J=3.5 Hz, 1H), 4.94 (s br, 1H), 5.10 (s, 1H); $^{13}$C-NMR (125 MHz, DMSO-d$_6$) δ 18.0, 18.6, 20.6, 21.7, 21.8, 23.0, 25.5, 28.1, 30.6, 32.5, 33.2, 34.4, 34.8, 35.2, 39.6, 43.6, 46.2, 46.3, 50.2, 51.8, 59.7, 60.6, 66.3, 70.7, 71.9, 72.1, 73.1, 74.4, 79.7, 95.2, 103.6, 106.6, 127.1, 138.9, 150.2, 155.8, 174.9.

EXAMPLE 4

Preparation of Ascosteroside Mono-p-bromobenzoate

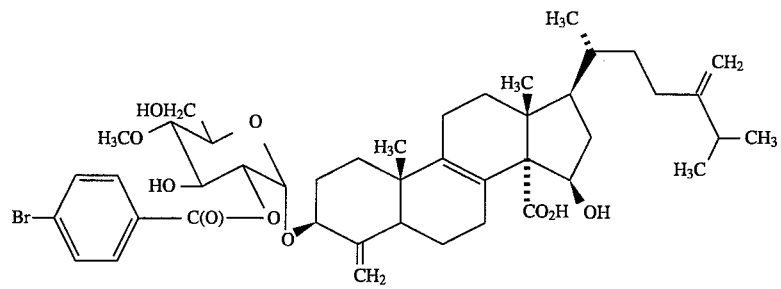

Ascosteroside (10 mg, 0.015 mmol) was dissolved in 1 mL chloroform and mixed with 4 equivalents dimethylaminopyridine (8 mg) and 4 equivalents p-bromobenzoyl chloride (13.5 mg). The contents were stirred at room temperature for 18 hours. Purification of the crude product by silica gel preparative TLC (0.5 mm Merck plate) using chloroform-methanol 9:1 as the developing solvent afforded ascosteroside mono-p-bromobenzoate (2.0 mg): C$_{44}$H$_{61}$O$_{10}$Br: TLC R$_f$ 0.28 (CHCl$_3$—MeOH 9:1); HRFABMS m/z 851.3324 ([M+Na]$^+$; calcd 851.3346); $^1$H-NMR (300 MHz, CDCl$_3$) δ 0.86 (s, 3H), 0.91 (d, J=6.1 Hz, 3H), 0.99 (d, J=6.8 Hz, 3H), 1.00 (d, J=6.8 Hz, 3H), 1.09 (s, 3H), 1.10–2.30 (broad envelope, 20H), 2.70 (m, 1H), 2.80 (m, 1H), 3.36 (t, J=9.3 Hz, 1H), 3.61 (s, 3H), 3.76 (m, 2H), 3.90 (m, 1H), 4.30 ( t, J=9.3 Hz, 1H), 4.53 (d, J=6.9 Hz, 1H), 4.63 (s, 1H), 4.67 (S, 1H), 4.70 (s, 1H), 4.87 (dd, J=3.6, 10.0 Hz, 1H), 5.19 (s, 1H), 5.29 (d, J=3.7 Hz, 1H), 7.58 (d, j=8.5 Hz, 2H), 7.91 (d, J=8.5 Hz, 2H).

EXAMPLE 5

Preparation of Ascosteroside Aglycone

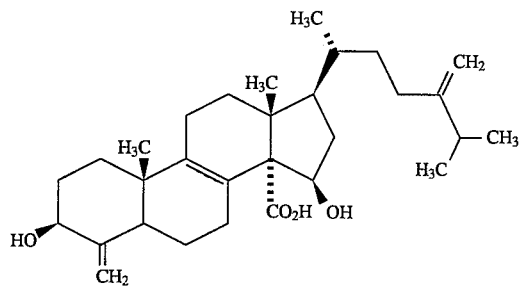

Ascosteroside (5 mg, 0.007 mmol) was dissolved in 1 mL 2.5M methanolic HCl, and the solution heated to 85° C. in a sealed vial for 20 hours. Purification of the product by silica gel preparative TLC (0.5 mm Merck plate) using chloroform-methanol 95:5 as the developing solvent afforded ascosteroside aglycone (0.8 mg): C$_{30}$H$_{46}$O$_4$; TLC R$_f$ 0.51 (CHCl$_3$—MeOH 95:5); HRFABMS m/z 493.3309 [M+Na]$^+$; calcd 493.3294; IONSPRAY LC-MS m/z 471 [M+H]$^+$.

What is claimed is:.

1. A compound having a structure of formula I:

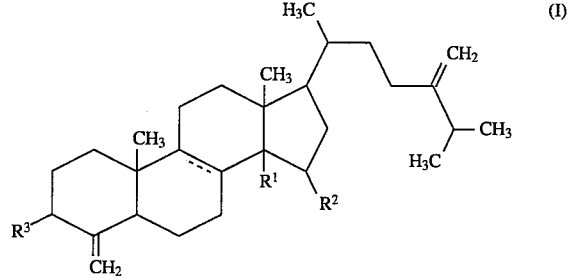

(I)

wherein

R$^1$ is —C(O)—OR$^4$, —C(O)N(R$^4$)$_2$ or —PO$_4$(R$^4$)$_2$;

R$^2$ is hydroxyl, —O—C(O)—R$^5$, —PO$_4$(R$^4$)$_2$ or —SO$_4$(R$^4$);

R$^3$ is hydroxyl, —O—C(O)—R$^5$, —PO$_4$(R$^4$)$_2$, —SO$_4$(R$^4$) or a sugar moiety;

each R$^4$ is independently hydrogen, alkyl or aryl;

each R$^5$ is independently alkyl or aryl; and the dotted line denotes an optional double bond;

or a salt or prodrug thereof.

2. The compound of claim 1 which is ascosteroside.

3. The compound of claim 1 which is ascosteroside methyl ester, ascosteroside mono-p-bromobenzoate, or ascosteroside aglycone.

4. A method for preventing or treating infection of a host by a fungus, comprising the step of administering to said host a compound of claim 1 which is physiologically tolerated by said host, in an amount effective for said prevention or treatment.

5. An antifungal pharmaceutical composition, comprising a compound of formula I of claim 1, or a physiologically tolerated salt or prodrug thereof, in an amount effective therefor, and a physiologically tolerated vehicle or diluent.

6. A method for inhibiting the growth of at least one fungus present on a surface or in a medium, comprising the step of contacting said surface or medium with a compound of the formula I of claim 1 or a salt thereof, in an amount effective for said inhibition.

7. A composition for the inhibition of fungal growth, comprising a compound of formula I of claim 1 or a salt thereof, in an amount effective therefor, and a vehicle or diluent.

8. The compound of claim 1 which is pure or substantially pure.

* * * * *